(12) United States Patent
Charlton et al.

(10) Patent No.: US 8,124,014 B2
(45) Date of Patent: Feb. 28, 2012

(54) AUTO-CALIBRATION CIRCUIT OR LABEL AND METHOD OF FORMING THE SAME

(75) Inventors: Steven C. Charlton, Osceola, IN (US); Joseph E. Perry, Osceola, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 276 days.

(21) Appl. No.: 12/473,187

(22) Filed: May 27, 2009

(65) Prior Publication Data

US 2009/0301166 A1 Dec. 10, 2009

Related U.S. Application Data

(60) Provisional application No. 61/131,474, filed on Jun. 9, 2008.

(51) Int. Cl.
*G01N 27/00* (2006.01)
(52) U.S. Cl. ............... 422/64; 422/62; 422/63; 422/65
(58) Field of Classification Search .............. 422/64, 422/62, 63, 65
See application file for complete search history.

(56) References Cited

U.S. PATENT DOCUMENTS

| | | | |
|---|---|---|---|
| 5,266,179 | A | 11/1993 | Nankai et al. |
| 5,366,609 | A | 11/1994 | White et al. |
| 5,575,403 | A | 11/1996 | Charlton et al. |
| 5,597,532 | A | 1/1997 | Connolly |
| 5,628,890 | A | 5/1997 | Carter et al. |
| 5,630,986 | A | 5/1997 | Charlton et al. |
| 5,700,695 | A | 12/1997 | Yassinzadeh et al. |
| 5,738,244 | A | 4/1998 | Charlton et al. |
| 5,810,199 | A | 9/1998 | Charlton et al. |
| 5,854,074 | A | 12/1998 | Charlton et al. |
| 6,102,872 | A | 8/2000 | Doneen et al. |
| 6,531,040 | B2 | 3/2003 | Musho et al. |

(Continued)

FOREIGN PATENT DOCUMENTS

EP 0 840 122 A2 5/1998

(Continued)

OTHER PUBLICATIONS

PCT Search Report for International Application No. PCT/US2009/046347 dated Oct. 14, 2009 (6 pages).

(Continued)

*Primary Examiner* — Jill Warden
*Assistant Examiner* — Monique Cole
(74) *Attorney, Agent, or Firm* — Nixon Peabody LLP

(57) ABSTRACT

An auto-calibration circuit or label is adapted to be used with an instrument. The instrument is adapted to determine information related to an analyte of a fluid sample. The auto-calibration circuit or label comprises a plurality of electrical connections, first and second common connections, and first and second auxiliary common connections. The electrical connections convey auto-calibration information corresponding to a test sensor. The auto-calibration information is adapted to be utilized by the instrument to auto-calibrate for the test sensor. The electrical connections include first contact areas. The second common connection is separate and distinct from the first common connection. The first auxiliary common connection is separate and distinct from the first and second common connections. The second auxiliary common connection is separate and distinct from the first and second common connections. The first and second auxiliary common connections are located on opposing sides of the contact areas. The electrical connections are adapted to be routed directly from each of the plurality of first contact areas to a respective first or a second common connection.

20 Claims, 10 Drawing Sheets

U.S. PATENT DOCUMENTS

| | | |
|---|---|---|
| 7,212,925 B2 | 5/2007 | Genshaw |
| 7,316,929 B2 | 1/2008 | Purcell |
| 7,875,240 B2 | 1/2011 | Perry et al. |
| 7,919,045 B2 | 4/2011 | Perry et al. |
| 7,939,019 B2 | 5/2011 | Edelbrock |
| 2009/0030617 A1 | 1/2009 | Schell et al. |
| 2009/0041625 A1 | 2/2009 | Perry et al. |
| 2009/0042306 A1 | 2/2009 | Reynolds et al. |
| 2009/0050491 A1 | 2/2009 | Brown |
| 2009/0113981 A1 | 5/2009 | Beer |
| 2009/0205399 A1 | 8/2009 | Sun et al. |
| 2009/0288964 A1 | 11/2009 | Jung et al. |
| 2010/0017165 A1 | 1/2010 | Zhong |
| 2010/0255567 A1 | 10/2010 | Lieber et al. |
| 2011/0011151 A1 | 1/2011 | Cheal |

FOREIGN PATENT DOCUMENTS

| | | |
|---|---|---|
| EP | 1 024 358 | 8/2000 |
| EP | 1 174 716 | 7/2001 |
| EP | 1 288 653 | 3/2003 |
| EP | 1 398 631 | 3/2004 |
| EP | 1 431 758 | 6/2004 |
| EP | 0 840 122 B1 | 9/2004 |
| JP | 2000-19147 | 1/2000 |
| WO | WO 2004/113911 | 12/2004 |
| WO | WO 2004/113915 | 12/2004 |
| WO | WO 2006/113721 | 10/2006 |
| WO | WO 2006/113865 | 10/2006 |
| WO | WO 2006/127635 | 11/2006 |

OTHER PUBLICATIONS

PCT Written Opinion for International Application No. PCT/US2009/046347 dated Oct. 14, 2009 (6 pages).

AUTO-CALIBRATION CIRCUIT OR LABEL AND METHOD OF FORMING THE SAME

CROSS-REFERENCE TO RELATED APPLICATION

This application claims the benefit of U.S. Provisional Patent Application No. 61/131,474, filed Jun. 9, 2008 entitled "Auto-Calibration Circuit Or Label And Method Of Forming The Same", which is hereby incorporated by reference in its entirety.

FIELD OF THE INVENTION

The present invention generally relates to an auto-calibration circuit or label and methods of forming the same. The auto-calibration circuit or labels are used in automatically calibrating instruments or meters that determine information related to an analyte (e.g., glucose concentration) in a fluid sample.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measures output. Optical systems may also test sensors that determine information related to an analyte (e.g., glucose concentration) in a fluid sample.

Diagnostic systems, such as blood-glucose testing systems, typically calculate the actual glucose value based on a measured output and the known reactivity of the reagent-sensing element (test sensor) used to perform the test. The reactivity or lot-calibration information of the test sensor may be given to the user in several forms including a number or character that they enter into the instrument. One prior art method included using an element that is similar to a test sensor, but which was capable of being recognized as a calibration element by the instrument. The test element's information is read by the instrument or a memory element that is plugged into the instrument's microprocessor board for directly reading the test element.

These methods suffer from the disadvantage of relying on the user to enter the calibration information, which some users may not do. In this event, the test sensor may use the wrong calibration information and thus return an erroneous result. It is would thus be desirable to provide the meter or instrument the calibration information automatically such that the user would not need to enter this information. It would be desirable to provide a device and method that provides additional auto-calibration information such as expiration date, date and time of the meter, and/or geographical (market) information.

SUMMARY OF THE INVENTION

An auto-calibration circuit or label is adapted to be used with an instrument. The instrument is adapted to determine information related to an analyte of a fluid sample. According to one embodiment, the auto-calibration circuit or label comprises a plurality of electrical connections, first and second common connections, and first and second auxiliary common connections. The plurality of electrical connections conveys auto-calibration information corresponding to a test sensor. The auto-calibration information is adapted to be utilized by the instrument to auto-calibrate for the test sensor. The plurality of electrical connections includes a plurality of first contact areas. The second common connection is separate and distinct from the first common connection. The first auxiliary common connection is separate and distinct from the first and second common connections. The second auxiliary common connection is separate and distinct from the first and second common connections. The first and second auxiliary common connections are located on opposing sides of the plurality of contact areas. The plurality of electrical connections is adapted to be routed directly from each of the plurality of first contact areas to a respective first common connection or a second common connection.

According to one embodiment, a test sensor is adapted to determine information relating to an analyte of a fluid sample. The test sensor comprises a base, a second layer and an auto-calibration label or circuit. The second layer and the base assist in forming a channel to receive the fluid sample. The auto-calibration circuit or label is located on the base or the second layer. The auto-calibration circuit or label comprises a plurality of electrical connections, first and second common connections, and first and second auxiliary common connections. The plurality of electrical connections conveys auto-calibration information corresponding to a test sensor. The auto-calibration information is adapted to be utilized by the instrument to auto-calibrate for the test sensor. The plurality of electrical connections includes a plurality of first contact areas. The second common connection is separate and distinct from the first common connection. The first auxiliary common connection is separate and distinct from the first and second common connections. The second auxiliary common connection is separate and distinct from the first and second common connections. The first and second auxiliary common connections are located on opposing sides of the plurality of contact areas. The plurality of electrical connections is adapted to be routed directly from each of the plurality of first contact areas to a respective first common connection or a second common connection.

In another embodiment, a sensor package is adapted to be used in an instrument or meter to determine information relating to an analyte in a fluid sample. The sensor package comprises at least one test sensor and an auto-calibration circuit or label. The at least one test sensor is adapted to receive the fluid sample and being operable with the instrument. The auto-calibration circuit or label comprises a plurality of electrical connections, first and second common connections, and first and second auxiliary common connections. The plurality of electrical connections conveys auto-calibration information corresponding to a test sensor. The auto-calibration information is adapted to be utilized by the instrument to auto-calibrate for the test sensor. The plurality of electrical connections includes a plurality of first contact areas. The second common connection is separate and distinct from the first common connection. The first auxiliary common connection is separate and distinct from the first and second common connections. The second auxiliary common connection is separate and distinct from the first and second common connections. The first and second auxiliary common connections are located on opposing sides of the plurality of contact areas. The plurality of electrical connections is adapted to be routed directly from each of the plurality of first contact areas to a respective first common connection or a second common connection.

BRIEF DESCRIPTION OF THE DRAWINGS

FIG. 4b is a side view of the test sensor of FIG. 4a.

DETAILED DESCRIPTION OF ILLUSTRATED EMBODIMENTS

An instrument or meter in one embodiment uses a test sensor adapted to receive a fluid sample to be analyzed, and a processor adapted to perform a predefined test sequence for measuring a predefined parameter value. A memory is coupled to the processor for storing predefined parameter data values. Calibration information associated with the test sensor may be read by the processor before the fluid sample to be measured is received. Calibration information may be read by the processor after the fluid sample to be measured is received, but not after the information directed to the analyte has been determined. Calibration information is used in measuring the predefined parameter data value to compensate for different characteristics of test sensors, which can vary on a batch-to-batch basis. Variations of this process will be apparent to those of ordinary skill in the art from the teachings disclosed herein, including but not limited to, the drawings.

The calibration information referred to herein may be any information that is used by a meter or instrument to calibrate. For example, the calibration information may be a program auto-calibration number that relates to a slope, intercept and sensitivity to common interferants of calibration lines for the test-sensor lot or batch.

In addition to defining the calibration information, the present invention may define additional information that has value to the consumer. The present invention has an unexpectedly large amount of information that may be transferred from a test sensor or a test-sensor package to the instrument or meter. The test sensor or test-sensor package may provide expansion capability for future products such as, for example, when the test-sensor chemistries are modified. It is contemplated that other modifications may be implemented. In addition to the calibration information and expansion capability, additional features may be added. For example, information such as market or country information, expiration dates and types of analytes may be transferred from the test sensor or the test-sensor package to the instrument or meter. The expiration dates may be programmed in different intervals such as, for example, every 2 or 3 months. The expiration date may be used in combination with the date and time of the meter to provide a small, age-related or stress-related correction so as to assist in correcting for an average stability drift. The information may also include detecting counterfeit sensors.

Figure 1:
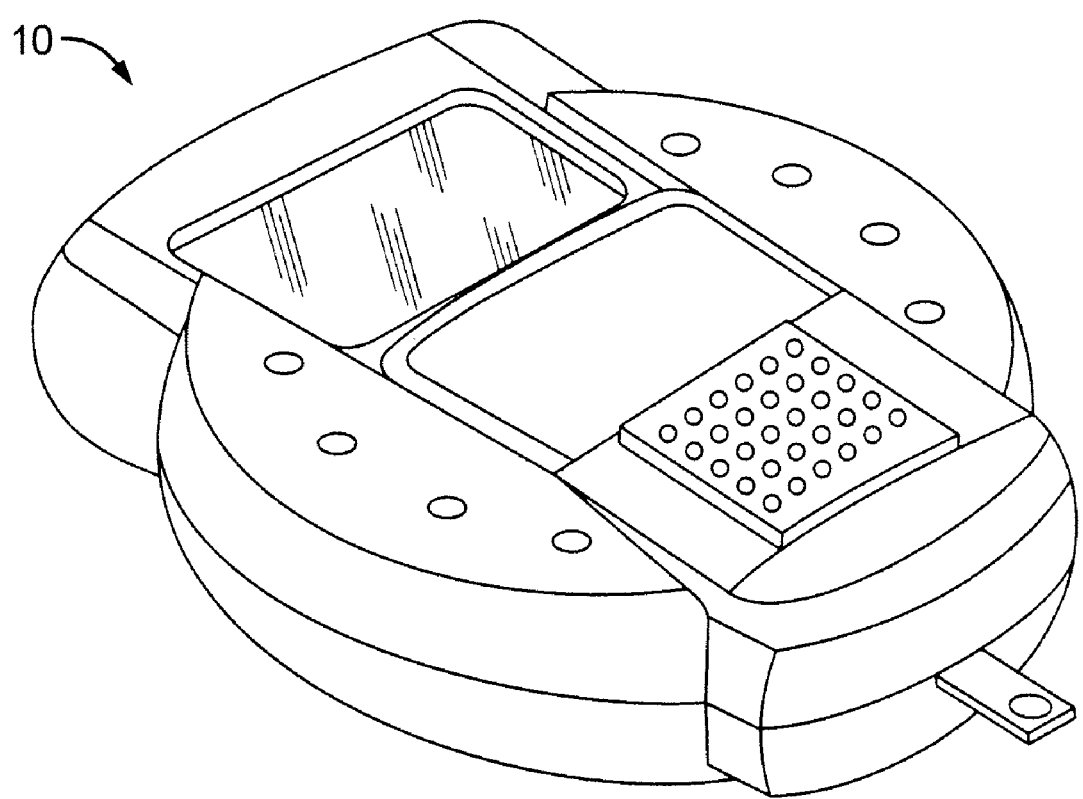
FIG. 1 shows a sensing instrument according to one embodiment.
Figure 2:
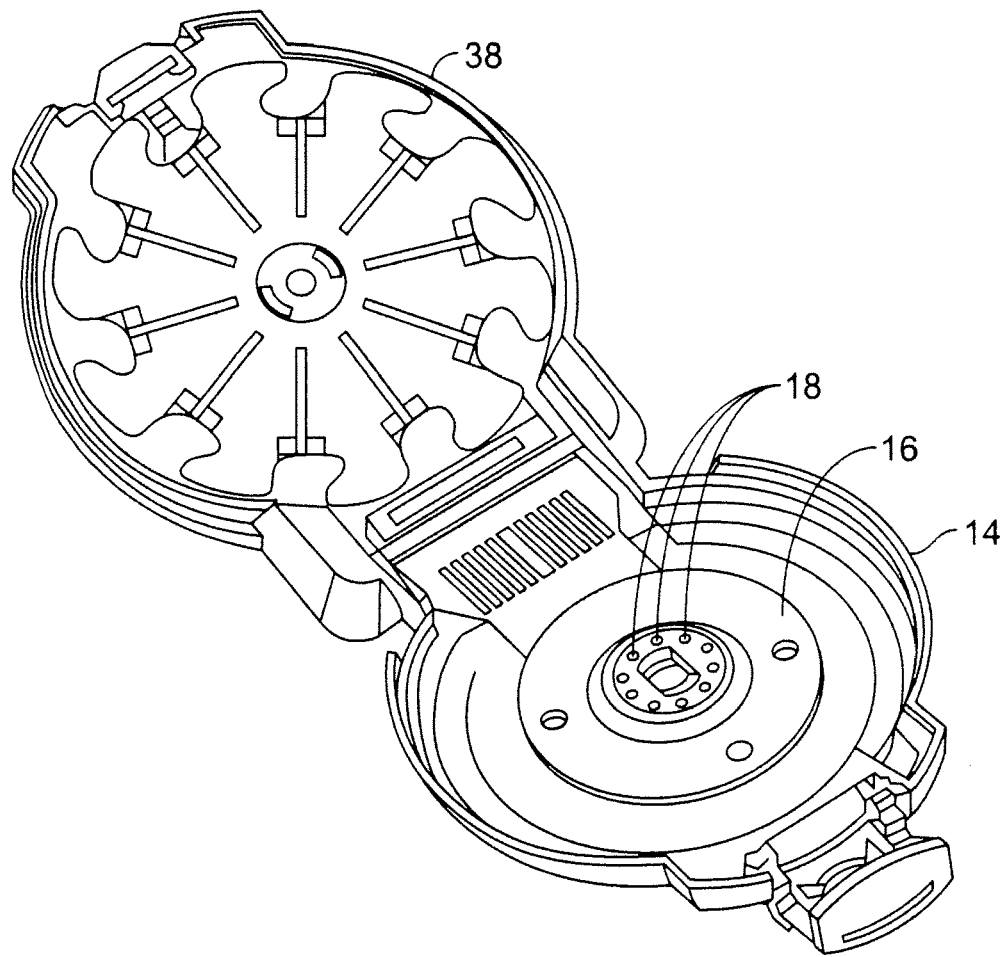
FIG. 2 shows the interior of the sensing instrument of FIG. 1.
Figure 3:
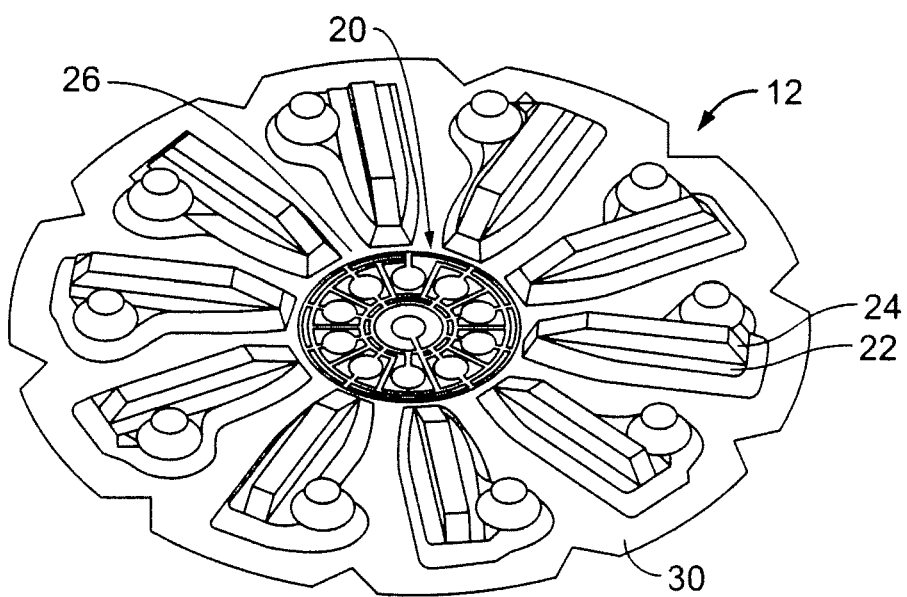
FIG. 3 shows a sensor package according to one embodiment for use with the sensing instrument of FIG. 2.

Referring now to FIGS. 1-3, an instrument or meter 10 is illustrated in one embodiment. In FIG. 2, the inside of the instrument 10 is shown in the absence of a sensor package. One example of a sensor package (sensor package 12) is separately illustrated in FIG. 3. Referring back to FIG. 2, a base member 14 of the instrument 10 supports an auto-calibration plate 16 and a predetermined number of auto-calibration pins 18. As shown in FIG. 2, for example, the instrument 10 includes ten auto-calibration pins 18. It is contemplated that the number of auto-calibration pins may vary in number and shape from that shown in FIG. 2. The auto-calibration pins 18 are connected for engagement with the sensor package 12.

The sensor package 12 of FIG. 3 includes an auto-calibration circuit or label 20 and a plurality of test sensors 22. The plurality of test sensors 22 is used to determine information related to an analyte (e.g., analyte concentrations). Analytes that may be measured include glucose, lipid profiles (e.g., cholesterol, triglycerides, LDL and HDL), microalbumin, hemoglobin $A1_C$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

The sensor package 12 contains a plurality of sensors 22 operable with the instrument 10. The plurality of sensors 22 typically has the same calibration characteristics such that calibrating the instrument 10 for one of the sensors 22 is effective to calibrate the instrument 10 for each of the plurality of sensors 22 in that particular package 12.

In one embodiment, the plurality of test sensors 22 includes an appropriately selected enzyme to react with the desired analyte or analytes to be tested. An enzyme that may be used to react with glucose is glucose oxidase. It is contemplated that other enzymes may be used to react with glucose such as glucose dehydrogenase. It is contemplated that other enzymes may be used to react with another analytes.

Calibration information or codes assigned for use in the clinical-value computations to compensate for manufacturing variations between sensor lots are encoded on the auto-calibration circuit or label 20 in this embodiment. The auto-calibration circuit or label 20 is used to automate the process of transferring calibration information (e.g., the lot specific reagent calibration information for the plurality of test sensors 22). The auto-calibration pins 18 electrically couple with the auto-calibration circuit or label 20 when a cover 38 of the instrument 10 is closed and the circuit or label 20 is present. The auto-calibration circuit or label 20 will be discussed in detail in connection with FIG. 7.

According to one method, an analyte concentration of a fluid sample is determined using electrical current readings and at least one equation. In this method, equation constants are identified using the calibration information or codes from the auto-calibration circuit or label 20. These constants may be identified by, for example, (a) using an algorithm to calculate the equation constants or (b) retrieving the equation constants from a lookup table for a particular predefined calibration code that is read from the auto-calibration circuit or label 20. The auto-calibration circuit or label 20 may be implemented by digital or analog techniques. In a digital implementation, the instrument may assist in determining whether there is conductance along selected locations to determine the calibration information. In an analog implementation, the instrument may assist in measuring the resistance along selected locations to determine the calibration information.

Referring back to FIG. 3, the plurality of test sensors 22 is arranged around the auto-calibration circuit or label 20 and extends radially from the area containing the circuit or label 20. The plurality of sensors 22 of FIG. 3 is stored in individual cavities or blisters 24 and read by associated sensor electronic circuitry before one of the test sensors 22 is used. The plurality of sensor cavities or blisters 24 extends toward a peripheral edge of the sensor package 12. In this embodiment, each sensor cavity 24 accommodates one of the test sensors 22.

The sensor package 12 of FIG. 3 is generally circular in shape with the sensor cavities 24 extending from near the outer peripheral edge toward and spaced apart from the center of the sensor package 12. It is contemplated, however, that the sensor package may be of different shapes then depicted in FIG. 3. For example, the sensor package may be a square, rectangle, other polygonal shapes, or non-polygonal shapes including oval.

In addition to the sensor package, the circuit or label may be used on a single test-sensor system in another embodiment. The circuit or label functions in a similar manner except that the circuit or label is located on the test sensor itself as opposed to the sensor package that contains the test sensors.

Figure 4A:
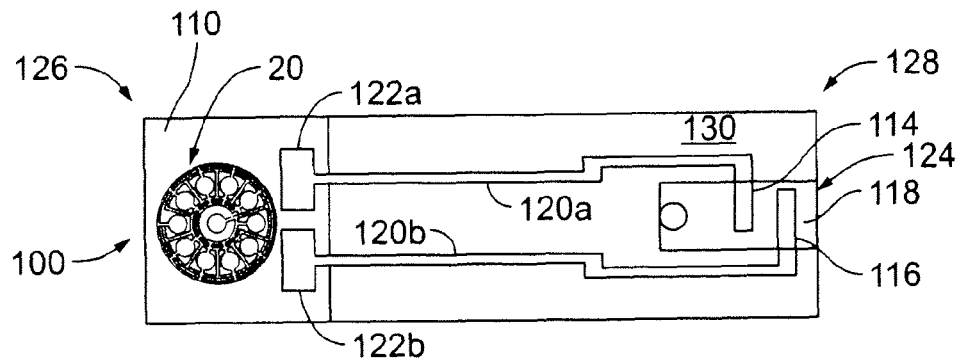
FIG. 4a is a test sensor according to one embodiment using the coded auto-calibration circuit or label of FIG. 7.

An example of a test sensor that includes the auto-calibration circuit or label 20 is depicted in FIG. 4a. FIG. 4a depicts a test sensor 100 that includes the auto-calibration circuit or label 20 that will be discussed in more detail below in conjunction with FIG. 7. In one embodiment, the test sensor 100 is adapted to receive a fluid sample and is analyzed using an instrument or meter.

Figure 4B:
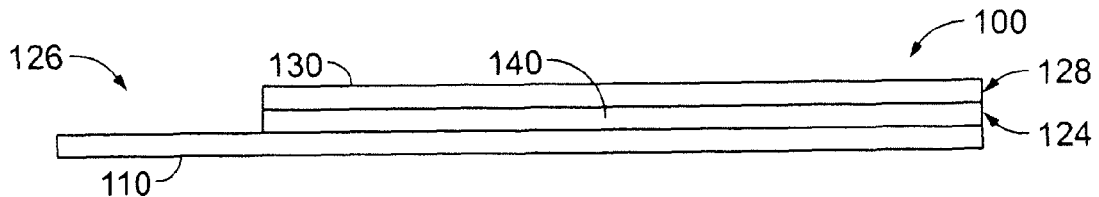

The test sensors described herein may be electrochemical test sensors. In such embodiments, the meter may have optical, electrochemical or mechanical aspects so as to detect the calibration information and electrochemical aspects to determine the analyte concentration of the fluid sample. One non-limiting example of an electrochemical test sensor is shown in FIGS. 4a, 4b. FIGS. 4a, 4b depict the test sensor 100 including a base 110, a channel (e.g., capillary channel), and a plurality of electrodes 114 and 116. The base and a second layer (e.g., a lid) assist in forming a channel (e.g., a capillary channel). A region 118 shows an area that defines the capillary channel (e.g., after a lid is placed over the base 110). The plurality of electrodes of FIG. 4a includes a counter electrode 114 and a working (measuring) electrode 116. The electrochemical test sensor may also contain at least three electrodes, such as a working electrode, an auxiliary or counter electrode, a trigger electrode, underfill detection electrode, or a hematocrit electrode. The electrodes 114, 116 are coupled to a plurality of conductive leads 120a, 120b, which, in the illustrated embodiment, terminate with a larger area designated as test-sensor contacts 122a, 122b. The capillary channel is generally located in a fluid-receiving area 124. It is contemplated that other electrochemical test sensors may be employed.

The fluid-receiving area 124 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

A fluid sample (e.g., blood) may be applied to the fluid-receiving area 124. The fluid sample reacts with the at least one reagent. After reacting with the reagent and in conjunction with the plurality of electrodes, the fluid sample produces electrical signals that assist in determining the analyte concentration. The conductive leads 120a, 120b carry the electrical signal back toward a second opposing end 126 of the test sensor 100 where the test-sensor contacts 122a, 122b transfer the electrical signals into the meter.

Referring specifically to FIG. 4b, a side view of the test sensor 100 of FIG. 4a is shown. As shown in FIG. 4b, the test sensor 100 of FIG. 1b further includes a lid 130 and a spacer 140. The base 110, the lid 130, and the spacer 140 may be made from a variety of materials such as polymeric materials. Non-limiting examples of polymeric materials that may be used to form the base 110, the lid 130, and the spacer 140 include polycarbonate, polyethylene terephthalate (PET), polyethylene naphthalate (PEN), polyimide, and combinations thereof. It is contemplated that other materials may be used in forming the base 110, lid 130, and/or spacer 140.

To form the test sensor 100 of FIGS. 4a, 4b, the base 110, the spacer 140, and the lid 130 are attached by, for example, an adhesive or heat sealing. When the base 110, the lid 130, and the spacer 140 are attached, a fluid-receiving area 124 is formed. The fluid-receiving area 124 provides a flow path for introducing the fluid sample into the test sensor 100. The fluid-receiving area 124 is formed at a first end or testing end 128 of the test sensor 100.

Figure 5:
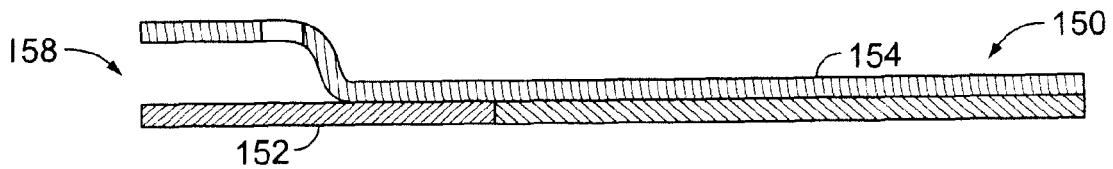
FIG. 5 is a cross-sectional view of a test sensor according to another embodiment.

It is contemplated that the test sensors may be formed with a base and a lid in the absence of a spacer. In one such embodiment, a lid may be formed with a convex opening that is adapted to receive a fluid. A non-limiting example of such a test sensor is shown in FIG. 5. Specifically, in FIG. 5, a test sensor 150 includes a base 152 and a lid 154. When the lid 154 is attached to the base 152, a fluid-receiving area 158 is formed that is adapted to receive fluid for testing.

The test sensors of the embodiments described herein may be optical test sensors. Optical test sensor systems may use techniques such as, for example, transmission spectroscopy, diffuse reflectance, or fluorescence spectroscopy for measuring the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid. The color change of the sample is evaluated to measure the absorbance level of the transmitted light.

Figure 6:
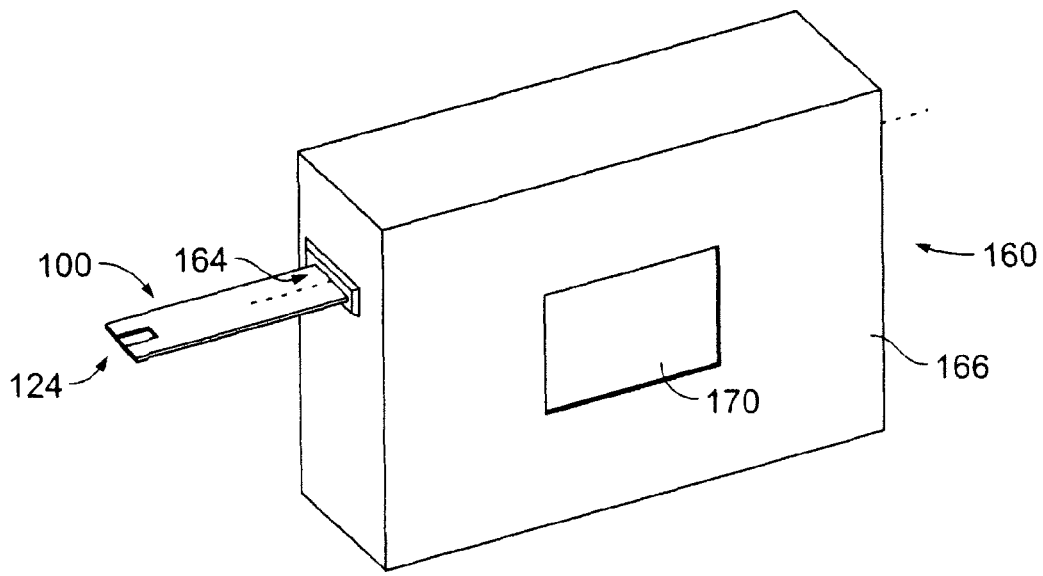
FIG. 6 is an isometric view of an instrument or meter for receiving the test sensors of FIGS. 4a, 5.

FIG. 6 depicts a single test-sensor instrument or meter 160. Referring back to FIGS. 4a, 4b, the second opposing end 126 of the test sensor 100 is adapted to be placed into a test-sensor opening 164 in the instrument or meter 160 of FIG. 6. The meter 160 includes a housing 166 that forms the test-sensor opening 164, which is of sufficient size to receive the second opposing end 126 of the test sensor 100. After the calibration information of the test sensor 100 has been determined, the meter 160 uses, for example, the appropriate program number during calculation of the analyte concentration by the meter software. The housing 166 may comprise a display 170 (e.g., an LCD screen) that displays, for example, analyte concentrations.

In the embodiments described herein, it is important that the test sensors are fully inserted into the test-sensor opening for the calibration information to be correctly ascertained. Thus, the meters used with the test sensors may include a mechanism for determining whether the test sensors are fully inserted. The mechanism may be positioned, for example, in or adjacent to the test-sensor opening. The meter may further be adapted to report an error to a user if it detects that the test sensor is not fully inserted.

An auto-calibration circuit or label comprises a plurality of electrical connections, a first common connection, a second common connection, a first auxiliary common connection and a second auxiliary common connection. The electrical connections convey auto-calibration information corresponding to a test sensor. The auto-calibration information is adapted to be utilized by an instrument to auto-calibrate for the test sensor. The plurality of electrical connections includes a plurality of first contact areas. The second common connection is separate and distinct from the first common connection. The first auxiliary common connection is separate and distinct from the first and second common connections. The second auxiliary common connection is separate and distinct from the first and second common connections. The first and second auxiliary common connections are located on opposing sides of the plurality of contact areas. The plurality of electrical connections is adapted to be routed directly from each of the plurality of first contact areas to a respective first common connection or a second common connection.

Figure 7:
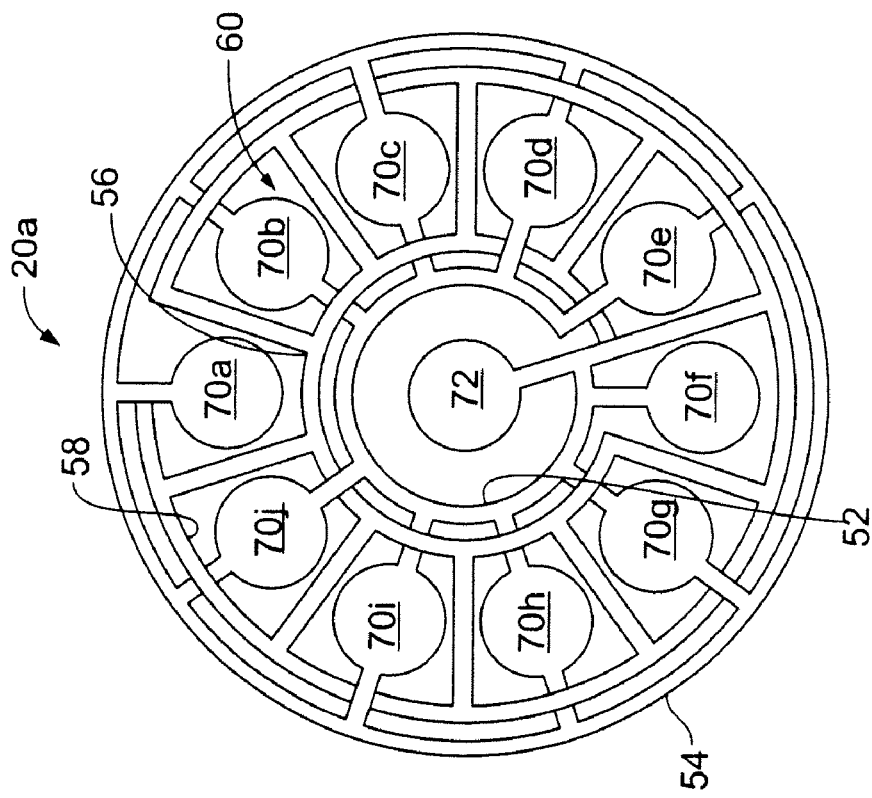
FIG. 7 shows a blank auto-calibrated circuit or label according to one embodiment.

With reference to FIG. 7, the auto-calibration circuit or label 20 is adapted to be used with a test-sensor package such as described above in FIGS. 1-3 or with test sensors such as described above in conjunction with FIGS. 4-6.

Specifically, the auto-calibration circuit or label 20 of FIG. 7 includes a first common connection (an inner ring 52), a second common connection (an outer ring 54), a first auxiliary common connection (an auxiliary inner ring 56), a second auxiliary common connection (an auxiliary outer ring 58) and a plurality of electrical connections (electrical connections 60). For some applications, the inner ring 52 represents logical 0s and the outer ring 54 represents logical 1s. It is contemplated that the inner ring or the outer ring may not be continuous. For example, the inner ring 52 as shown in FIG. 7 is not continuous because it does not extend to form a complete circle. The outer ring 54 as shown in FIG. 7, on the other hand, is continuous. The inner ring and the outer ring may both be continuous and in another aspect the inner ring and the outer ring are not continuous. It is contemplated that the inner ring and outer rings may be shapes other than circular. Thus, the term "ring" as used herein includes non-continuous structures and shapes other than circular.

The plurality of electrical connections 60 includes a plurality of contact areas or pads 70a-j. The plurality of contact areas 70a-j is radially positioned around the circumference of the auto-calibration circuit or label 20. It is contemplated that the plurality of contact areas 70a-j may be located in different positions than depicted in FIG. 7. The auto-calibration circuit or label 20 further includes a contact area or pad 72 that is located in the general center of the auto-calibration circuit or label 20.

In the embodiment depicted in FIG. 7, the plurality of electrical connections 60 are capable to be routed directly from each of the plurality of contact areas 70 to a respective first common connection (e.g., inner ring 52) or a second common connection (e.g., outer ring 54). The information from the plurality of electrical connections 60 corresponds to the calibration information of the test sensor(s) to be used by the instrument or meter.

According to one aspect, substantially all of the plurality of outer contact areas 70a-j are initially electrically connected to the first common connection (e.g., inner ring 52) and the second common connection (e.g., outer ring 54) in the auto-calibration circuit or label 20 of FIG. 7. To program the auto-calibration label, substantially all of the outer contact areas 70a-j in this embodiment are desirably only be connected to one of the inner or outer rings 52, 54.

FIG. 7 does not depict a specific pattern, but rather shows a number of the potential connections of the plurality of contact areas 70a-j to the first and second common connections. By using a blank auto-calibration circuit or label, the manufacturing process tends to be easier because it takes relatively little effort to encode as compared to creating a relatively complex fully encoded label from scratch. A common form of a blank label is one in which all contact areas are initially connected and specific connections are severed to form an encoded auto-calibration circuit or label. In another embodiment of a blank label, all contact areas can be initially disconnected and specific areas are connected during the encoding process.

Figure 8:
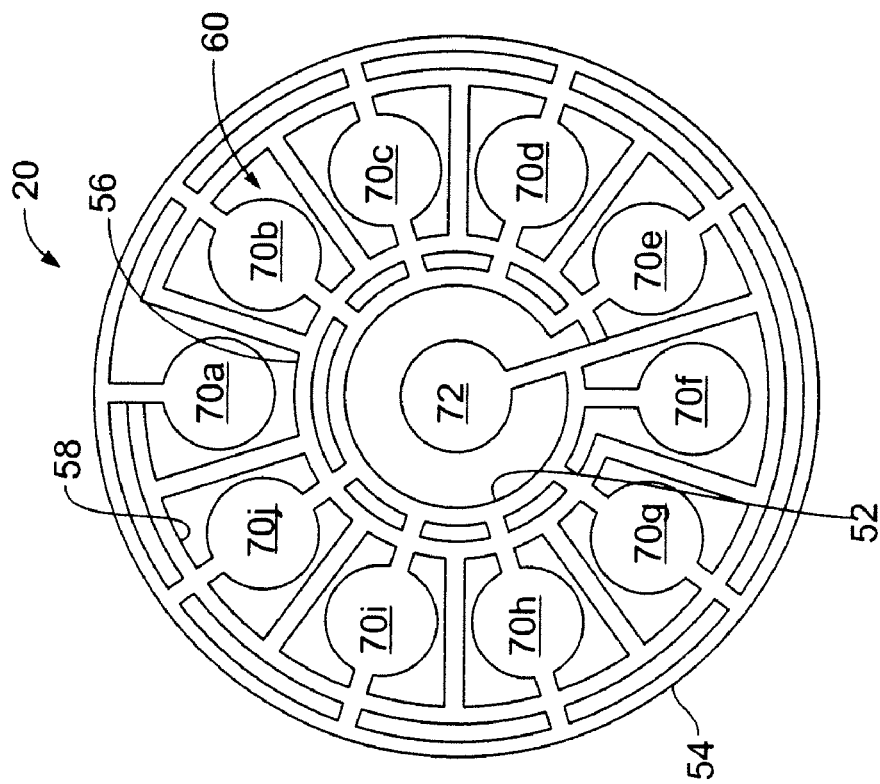
FIGS. 8-12 show coded auto-calibration circuits or labels according to various embodiments using the blank of FIG. 7.

One example of a pattern of the auto-calibration circuit or label 20 is shown in FIG. 8 with auto-calibration circuit or label 20a.

Typically, at least one of the contact areas 70 will always be electrically connected to the first common connection (e.g., inner ring 52) and a different one of the contact areas will be electrically connected to the second common connection (e.g., outer ring 54). For example, contact area 70a of FIGS. 7 and 8 is always electrically connected to the outer ring 54. Similarly, contact area 70f of FIGS. 7 and 8 is always electrically connected to the inner ring 52. By having individual contact areas only connected to the first common connection or the second common connection assists in maintaining a reliable instrument since any "no connect" may be sensed by the instrument software.

At least one of the contact areas 70 in one embodiment (e.g., contact areas 70b, 70h in FIG. 8) is isolated in that the contact area is not connected to any of the remaining contact areas 70. These contact areas 70b, 70h may act as starting points for the auto-calibration code because the instrument or meter does not know where the code begins or ends. Since two isolated contacts areas are used (contact areas 70b, 70h in FIG. 8), the spacing between these contact areas may be used as additional coding information. The distance between the isolated contact areas may be used, for example, to distinguish between different products. For example, if the isolated contact areas are directly adjacent to each other, then that may correspond to a first product. If the isolated contact areas are separated by one intervening contact area, then that may correspond to a second product. It is contemplated that the distance between the isolated contact areas may be used in another manner.

Referring still to FIG. 8, the remaining contact areas (contact areas 70c, 70d, 70e, 70g, 70i and 70j) are connected to either the first common connection (e.g., inner ring 52) or the second common connection (e.g., outer ring 54). Specifically, as shown in FIG. 8, contact areas 70d, 70e, and 70j are connected to the inner ring 52. The contact areas 70c, 70g and 70i are connected to the outer ring 54. By having six contacts areas that may be connected to either the first or second common connection, this gives a possibility of up to $2^6$ or 64 additional combinations. If at least one contact area needs to be connected to the first common connection and another contact area needs to be connected to the second common connection, the combination is reduced to 62 additional combinations because if all six are connected to the first common connection, then there are no connections to the second common connection and if all six are connected to the second common connection then there are not connections to the first common connection.

To expand the additional combinations, an additional second contact area that can function in a different manner than the other first contact areas may be included. This second contact area may be used to significantly enhance the amount of auto-calibration information that can be transferred to the instrument or meter. In one aspect, the second contact areas may be connected to the first common connection, the second common connection, an isolated contact area, and/or connected to a plurality of isolated or no-contact areas.

For example, the contact area 72 of FIG. 8 may be connected to the inner ring 52, the outer ring 54, the no-contact area 70b, no-contact area 70h, or connected to both the no-contact areas 70b, 70h. By having the ability to connect to the contact area 72 to one of these five combinations increases the combinations from 64 to 320 (64×5) combinations to convey auto-calibration information. The number of combinations can also be increased be locating the no-contact areas adjacent to each or having one, two or three intermediate areas therebetween. In such a scenario, the combinations would be increased by a three-fold. The number of combinations can also be increased be varying the location of the area connected to the contact area 72 by any of the seven other contact areas 70, which would increase the combinations by a further six-fold.

In FIG. 8, the contact area 72 of the auto-calibration label or circuit 20a is connected with the contact area 70h via the auxiliary outer ring 58 and the auxiliary inner ring 56. By having auxiliary inner and outer rings 56, 58 radially located on opposing sides of the contact pads 70 provides redundant connects to the contact area 72. These redundant pathways allow a path around a contact area that is connected to the first and second common connections.

If the contact area 72 is connected to the second common connection, then the first and second auxiliary common connections may not be connected to the second common connection. Similarly, if the contact area 72 is connected to the first common connection, then the first and auxiliary common connections may not be connected to the first common connection. In these methods, regardless of whether a contact area 70 is connected to the first or second common connection, the contact area 70 may be connected to the contact area 72.

Figure 9:
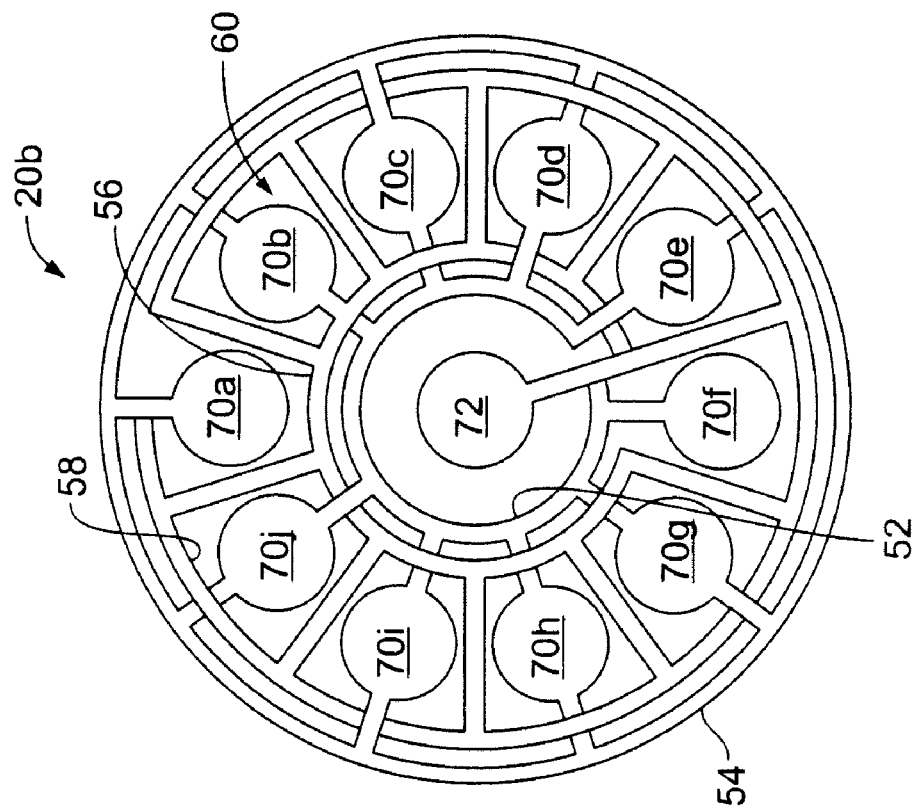

It is contemplated that other patterns of the auto-calibration circuit or label may be formed from the blank auto-calibration circuit or label 20 of FIG. 7. For example, in FIG. 9, an auto-calibration circuit or label 20b is depicted that includes the contact area 72 being connected to the no-contact area 70b via the auxiliary outer ring 58 and the auxiliary inner ring 56. The auto-calibration circuit or label 20b is similar to the auto-calibration circuit or label 20a of FIG. 8 except that the auto-calibration circuit or label 20a has the contact area 72 being connected to the no-contact area 70h.

Figure 10:
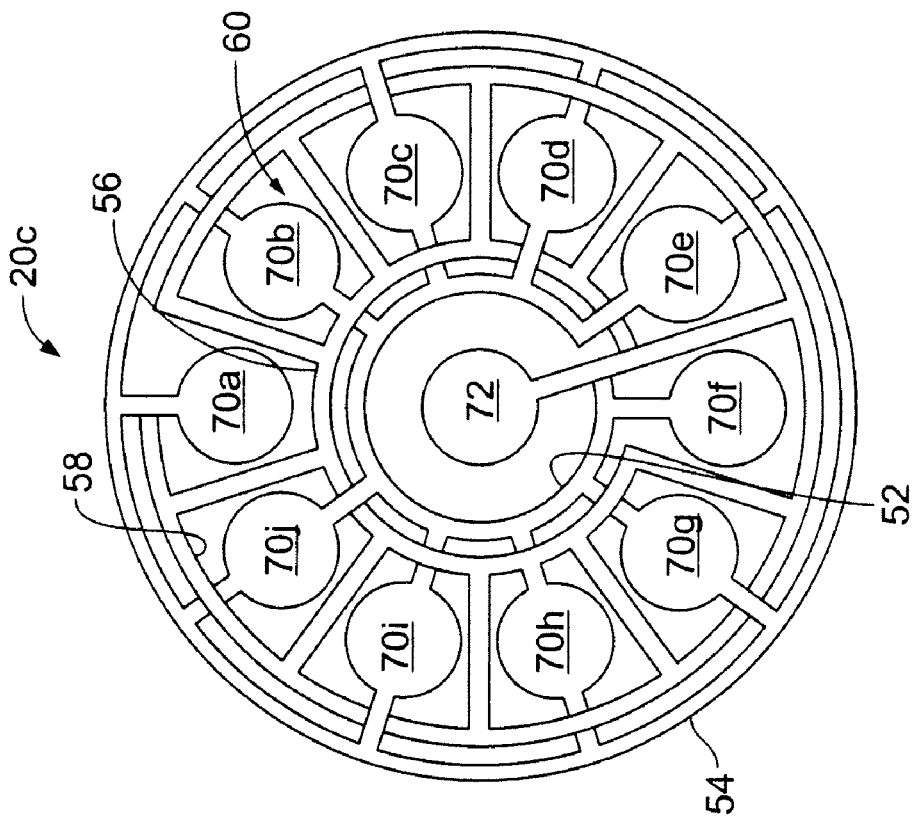

In addition, the two no-contact areas 70b, 70h may be connected to each other. This is shown, for example, in FIG. 10 with an auto-calibration circuit or label 20c being depicted that includes the contact area 72 being connected to the no-contact areas 70b, 70h via the auxiliary outer ring 58 and the auxiliary inner ring 56. It is also contemplated that additional no-contact areas may be used in the forming the auto-calibration circuit or area.

Figure 12:
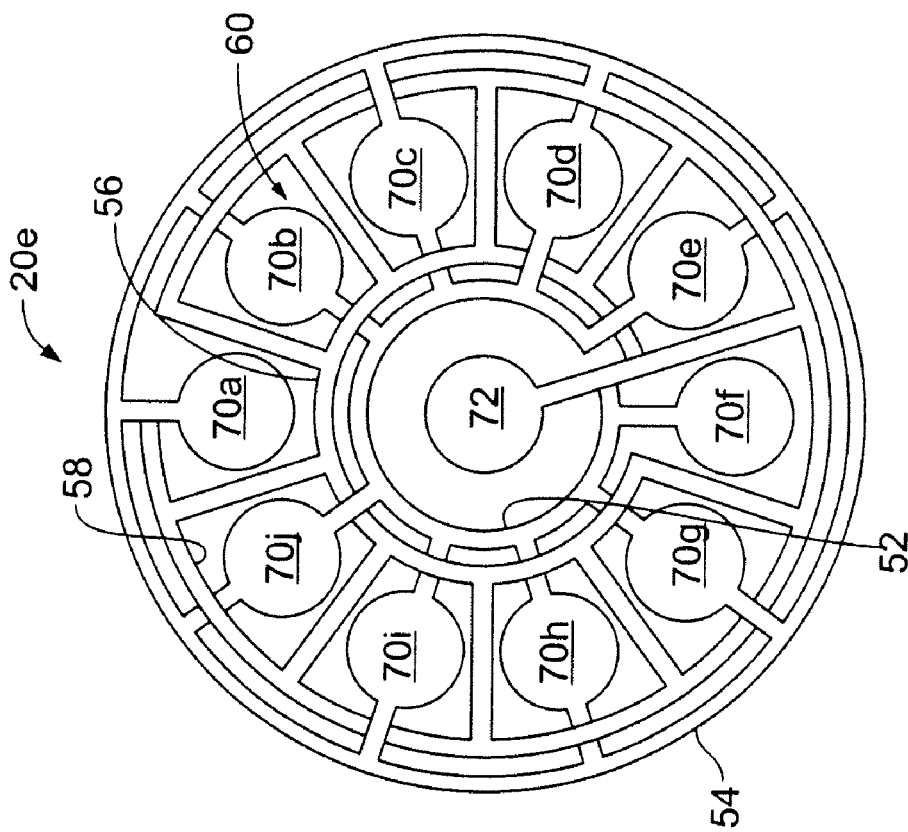
Figure 11:
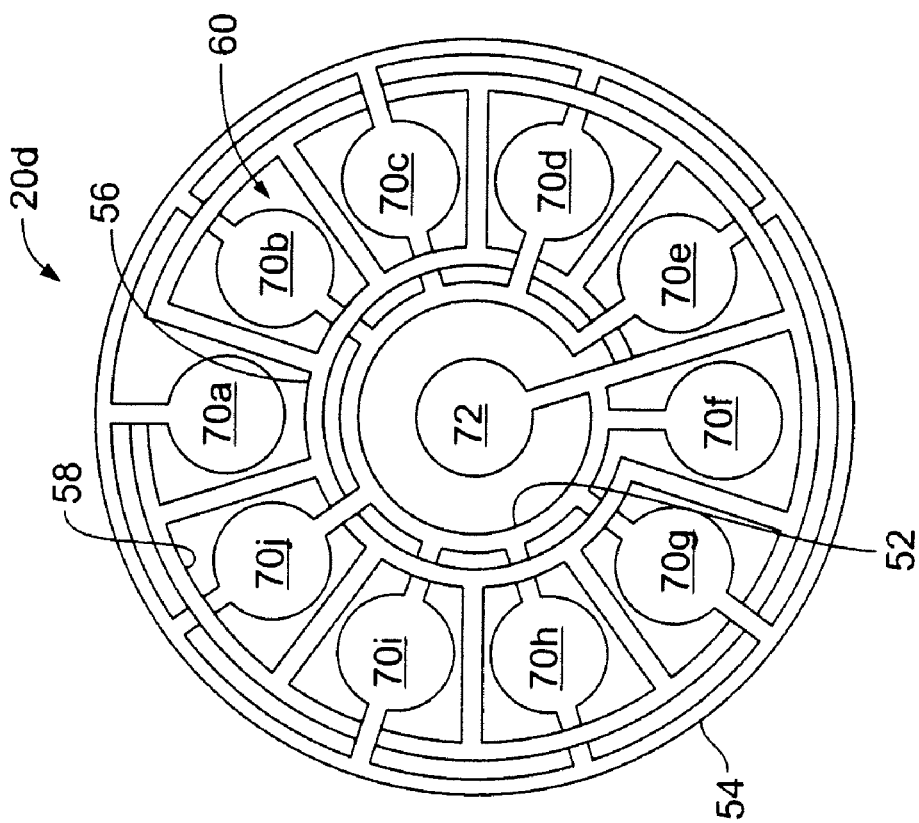

Referring to FIG. 11, an auto-calibration circuit or label 20d is depicted that includes the contact area 72 being connected to the inner ring 52. Referring to FIG. 12, an auto-calibration circuit or label 20e is depicted that includes the contact area 72 being connected to the outer ring 54.

The instrument may include several responses to reading the auto-calibration label. For example, responses may include the following codes: (1) correct read, (2) misread, (3) non-read, defective code, (4) non-read, missing label, and (5) read code out-of-bounds. A correct read indicates that the instrument or meter correctly read the calibration information. A misread indicates that the instrument did not correctly read the calibration information encoded in the circuit or label. In a misread, the circuit or label passed the integrity checks. A non-read, defective code indicates that the instrument senses that a circuit or label is present (continuity between two or more auto-calibration pins), but the code fails one or more encoding rules (circuit integrity checks). A non-read, missing circuit or label indicates that the instrument does not sense the presence of a circuit or label (no continuity between any of the auto-calibration pins). A read code out-of-bounds indicates that the instrument senses an auto-calibration code, but the calibration information is not valid for that instrument.

The auto-calibration circuit or label (e.g., auto-calibration circuits or labels 20) to be used with an instrument may be formed according to the following method. A structure including an electrically conductive layer is provided. A pattern is created with the electrically conductive layer by printing or using a laser to form an auto-calibration label. The pattern is created in or through the electrically conductive layer using a laser. The pattern is adapted to be utilized by the instrument to auto-calibrate.

The electrically conductive layer may include conductive metals, conductive alloys, or conductive polymeric coatings. Non-limiting examples of conductive metals and conductive alloys that may be used include aluminum, copper, nickel, palladium, silver, stainless steel, titanium nitride, platinum, gold, or combinations thereof. It is contemplated that other conductive metals may be used in forming the electrically conductive layer. The thickness of the electrically conductive metal or conductive alloy in the electrically conductive layer may vary but generally is from about 1 to about 1,000 nm. More typically, the electrically conductive layer is from about 10 to about 250 nm.

Conductive polymeric coatings are defined herein as including at least one polymeric resin and conductive particles or flakes. It is contemplated that several types of polymeric materials may be used such as, for example, thermoplastics and thermosets. Non-limiting examples of conductive particles that may be used in the conductive polymeric coatings include aluminum, carbon, graphite, copper, nickel, palladium, silver, platinum, gold, or combinations thereof. It is contemplated that other conductive particles may be used in forming the electrically conductive polymeric coatings. The thickness of the electrically conductive polymeric coatings may vary but generally is from about 0.5 micron to about 500 microns. More typically, the thickness of the electrically conductive polymeric coatings is from about 5 to about 50 microns.

The conductive polymer coatings may be formed by a variety of methods. In one method, the conductive polymer coating is formed by screen printing. In another method, the conductive polymer coating is formed by gravure printing. In a further method, the conductive polymer coating is produced onto the polymer substrate by a variety of standard coating techniques such as, for example, reverse roll, Meyer rod, doctor blade, slot die, direct gravure, offset gravure, reverse gravure, differential speed offset gravure, nip and pan feed, knife-over roll or spray coating.

In one aspect, the structure consists of the electrically conductive layer such as, for example, a single layer of aluminum or nickel. In another embodiment, the structure includes a polymeric portion (e.g., polymeric film) and a metallic portion. For example, the structure may be a metalized polymeric film, a coextruded metalized polymeric film, or a laminated metalized polymeric film. It is contemplated that other structures may be employed in the methods of the present invention. The polymeric portion to be used in these structures may be formed from a variety of polymeric materials or filled-polymeric materials. The polymeric portion may have a rough or textured surface in one embodiment. The polymeric portion may have a smooth surface in another embodiment. For example, the polymeric portion may be made from materials such as polyethylene, polypropylene, oriented polypropylene (OPP), cast polypropylene (CPP), polyethylene terephthlate (PET), polyether ether ketone (PEEK), polyether sulphone (PES), polycarbonate, or combinations thereof. The thickness of the polymeric film is generally from about 6 to about 500 microns. More specifically, the thickness of the polymeric film is generally from about 25 to about 250 microns.

The metalized polymeric film may be formed by a variety of methods. In one method, the metalized polymeric film is formed by having metal sputtered on the polymeric film. In another method, the metalized polymeric film is formed by having metal vapor deposited on the polymeric film. In a further method, metal may be flashed onto the polymeric film. In another method, the metalized polymeric film may be formed by coextrusion or lamination. It is contemplated that other methods may be used in forming the metalized polymeric film to be used in the present invention.

The auto-calibration circuits may be formed completely or partially by a conductive ink printed in specific areas such as, for example, by using ink-jet technology. The conductive ink may be used to link existing contact areas of the electrically conductive layer, or to form the entire patterned conductive layer. A catalyst for electro-less plating may be printed instead of a conductive ink, and an autocalibration circuit is formed subsequently by electro-less plating the desired metal in the areas defined by the catalysis.

The auto-calibration circuits or labels (e.g., auto-calibration circuits or labels 20) may be formed and then attached to a sensor package (e.g., sensor package 12) or a test sensor (e.g., test sensor 100). The auto-calibration circuit or label may be attached to the sensor package or the test sensor via, for example, an adhesive or other attachment method.

In another method, the auto-calibration circuit or label may be formed directly on the sensor package (e.g., sensor package 12) or a test sensor (e.g., test sensor 100). For example, at least a portion of the surface of the sensor-package base or the test-sensor base includes an electrically conductive layer. The pattern is created with this electrically conductive layer using a laser. Thus, in this method the electrically conductive metal is part of the product packaging or the test sensor itself.

As shown in FIG. 7, some of the contact areas 70 are initially electrically connected to the first common connection (e.g., inner ring 52) and the second common connection (e.g., outer ring 54). In one method, to program the auto-calibration circuit or label, however, the conductive material (e.g., conductive ink) may be severed to break the electrical connection from the contact areas 70 to either the outer ring 54 or the inner ring 52 so that an individual contact area 70 is only connected to one of the inner or outer rings 52, 54.

One method for severing the conductive material is to break the electrical connection by using a laser cut. It is contemplated that other methods of breaking the electrical connection may be used such as punching holes through the circuit or label. It is also contemplated that the cuts may be formed according to other methods. It is also contemplated that appropriate "gaps" may be formed in the conductive material such that breaking the electrical connection by, for example, laser cutting is unnecessary or that the final, coded pattern be made directly without additional marking or severing steps.

A laser creates the pattern with the electrically conductive layer to form an auto-calibration label. The laser functions by cutting the electrically conductive layer in selected locations to form the desired auto-calibration circuit or label. There are many different types of lasers that may be used in creating the pattern on the electrically conductive layer. The lasers remove the electrically conductive layer to electrically isolate regions.

One laser that may be used in the present invention is a solid-state laser such as an yttrium-based laser. Examples of yttrium-based lasers that are commercially available are Rofin DY-HP Series, Telesis ECLIPSE® TLM, or Telesis ZENITH® Series. It is contemplated that other yttrium-based lasers may be used.

Another type of laser that may be used is a gas laser such as a carbon dioxide-based laser. Examples of carbon dioxide-based lasers that are commercially available are Rofin FA Series, Telesis SABRE® Series, or Keyence ML-G Series $CO_2$. It is contemplated that other carbon dioxide-based lasers may be used.

A further type of laser that may be used is an Excimer laser. Excimer lasers use reactive gases, such as chlorine and fluorine, that are mixed with inert gases such as argon, krypton or xenon. To obtain optimum ablation, the wavelength may need to be matched to the selected metal of the conductive layer. An example of an Excimer laser that is commercially available is Lambda Physik $F_2$ Series. It is contemplated that other Excimer lasers may be used. It is also contemplated that other lasers may be used in forming the auto-calibration circuits or labels of the present invention other than those discussed above in the specific examples above.

According to one method, the pattern may be created using a mask and a laser such as, for example, an Excimer laser or a carbon dioxide-based laser. It is contemplated that various masks may work in conjunction with the laser in forming the auto-calibration circuit or label. One example of a mask is a chrome-on-glass mask in which the beam of light is only allowed to pass through selected areas to form the auto-calibration circuit or label.

According to one method, the pattern may be created using direct writing of the lines. In this method, the laser beam of light is moved so as to form the desired pattern. It is contemplated that other patterns may be created using direct writing of the lines. Lasers that produce a beam of energy capable of removing the conductive layer and that can be moved to form a pattern may be used in this method. Non-limiting examples of such lasers are carbon dioxide-based lasers and yttrium-based lasers such as yttrium aluminum garnet (YAG) lasers.

Using lasers is desirable because they are adapted to work in tighter spaces. For example, these laser methods can produce spaces between adjacent electrical areas of from about 25 to about 250 microns, which allows for the possibility of tighter tolerances and/or a smaller auto-calibration area.

The auto-calibration circuits or labels 20 of FIGS. 7-11 are generally circular shaped. It is contemplated, however, that the auto-calibration circuits or labels may be of different shapes than depicted in FIGS. 7-11. For example, the auto-calibration circuit or label may be a square, rectangle, other polygonal shapes, and non-polygonal shapes including oval. This is shown, for example, with the auto-calibration circuit or labels 220*a-d* of FIGS. 13-16. The auto-calibration circuit or labels 220*a-d* function in a similar manner as that described above with respect to auto-calibration circuit or label 20.

Figure 13:
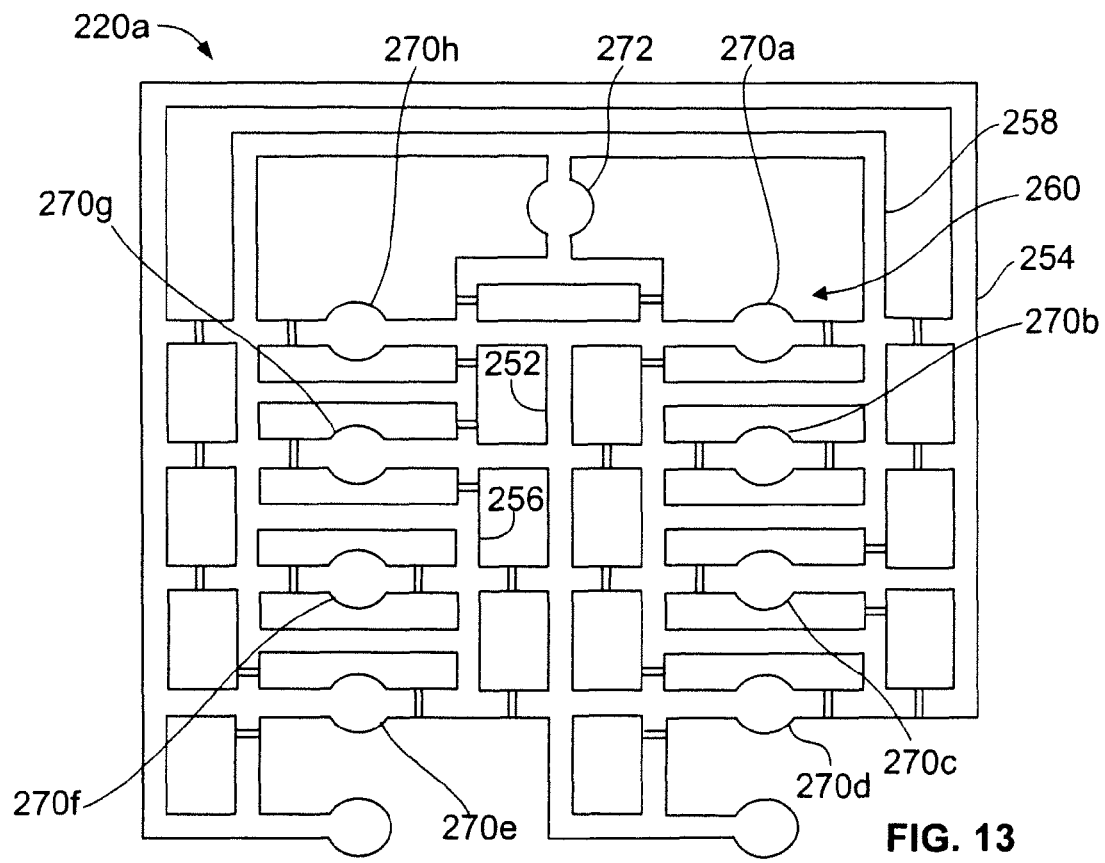
FIGS. 13-16 show coded auto-calibration circuits or labels according to one embodiment.

As shown in FIG. 13, the auto-calibration circuit or label 220*a* includes a first common connection (inner connection 252), a second common connection (an outer ring 254), a first auxiliary common connection (an auxiliary inner ring 256), a second auxiliary common connection (an auxiliary outer ring 258) and a plurality of electrical connections 260. The plurality of electrical connections 260 includes a plurality of contact areas or pads 270*a-h*. It is contemplated that the plurality of contact areas 270*a-h* may be located in different positions than depicted in FIG. 13. The auto-calibration circuit or label 220*a* further includes a contact area or pad 272 that is located in the upper center of the auto-calibration circuit or label 220*a* of FIG. 13.

In the embodiment depicted in FIG. 13, the electrical connections 260 are adapted to be routed directly from each of the plurality of contact areas 270 to a respective first common connection 252 or a second common connection 254. The information from the plurality of electrical connections 260 corresponds to the calibration information of the test sensor(s) to be used by the instrument or meter.

According to one aspect, substantially all of the plurality of outer contact areas 270*a-h* are initially electrically connected to the first common connection 252 or the second common connection 254 in the auto-calibration circuit or label 220*a* of FIG. 13.

At least one of the contact areas 270 in one embodiment (e.g., contact areas 270*b*, 270*f* in FIG. 13) is isolated in that the contact area is not connected to any of the remaining contact areas 270. Since two isolated contacts areas are used (contact areas 270*b*, 270*f* in FIG. 13), the spacing between these contact areas may be used as additional coding information. The distance between the isolated contact areas may be used, for example, to distinguish between different products. For example, if the isolated contact areas are directly adjacent to each other, then that may correspond to a first product. If the isolated contact areas are separated by one intervening contact area, then that may correspond to a second product. It is contemplated that the distance between the isolated contact areas may be used in another manner.

Referring still to FIG. 13, contact areas 270*a*, 270*d*, 270*g* and 270*h* are connected to the first common connection 252. The contact areas 270*c* and 270*e* are connected to the second common connection 254.

To expand the additional combinations, an additional second contact area that can function in a different manner than the other first contact areas may be included. This second contact area may be used to significantly enhance the amount of auto-calibration information that can be transferred to the instrument or meter. In one aspect, the second contact area may be connected to the first common connection, the second common connection, an isolated contact area, and/or connected to a plurality of isolated or no-contact areas. The second contact area may be connected to none of the other common connections and the isolated or no-contact areas.

For example, the contact area 272 may be connected to the first common connection 252, the second common connection 254, the isolated contact area 270*b*, the isolated contact area 270*f*, or connected to both the contact areas 270*b*, 270*f*. In FIG. 13, the contact area 272 is not connected to the first common connection 252, the second common connection 254, the isolated contact area 270*b*, or the isolated contact area 270*f*.

Figure 14:
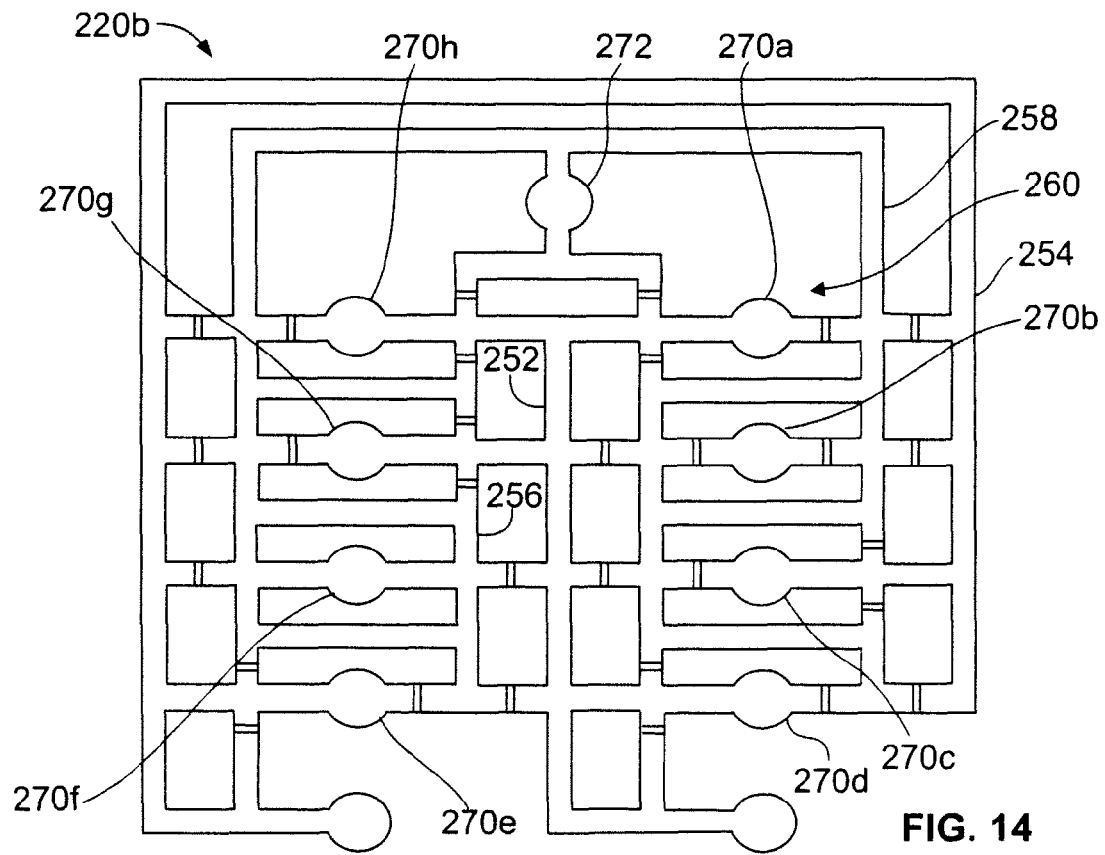
Figure 15:
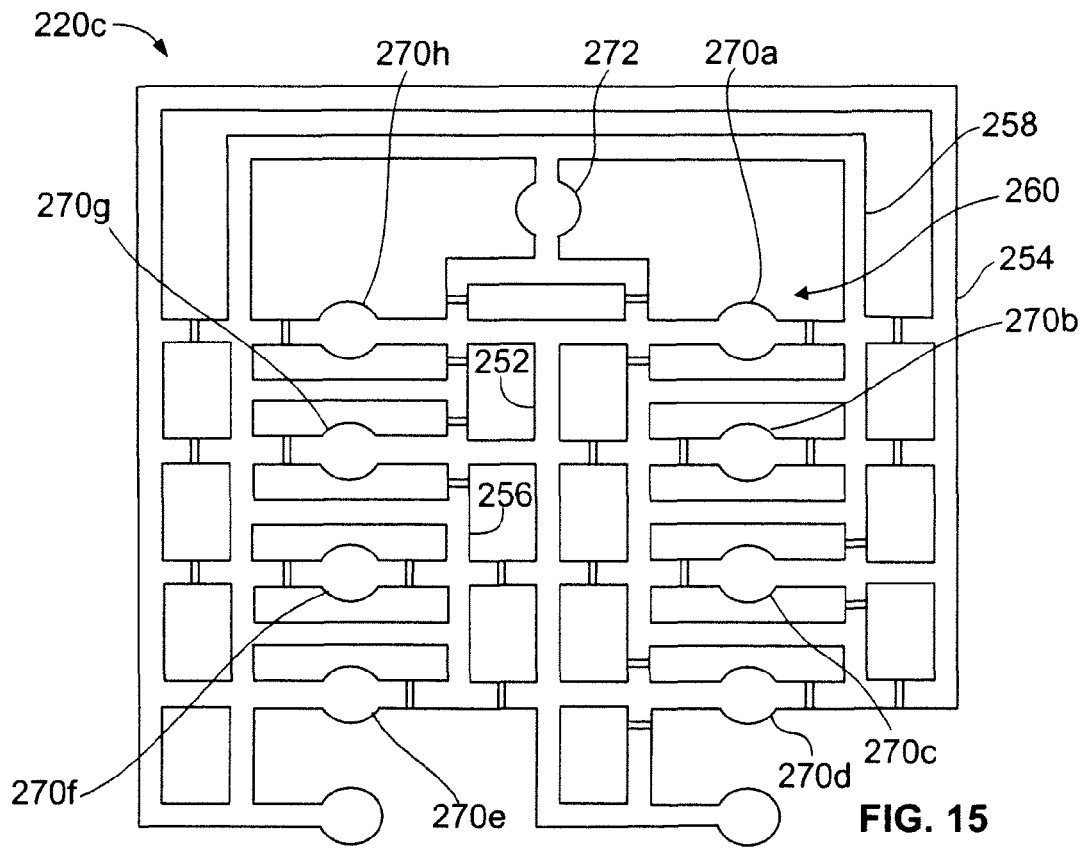
Figure 16:
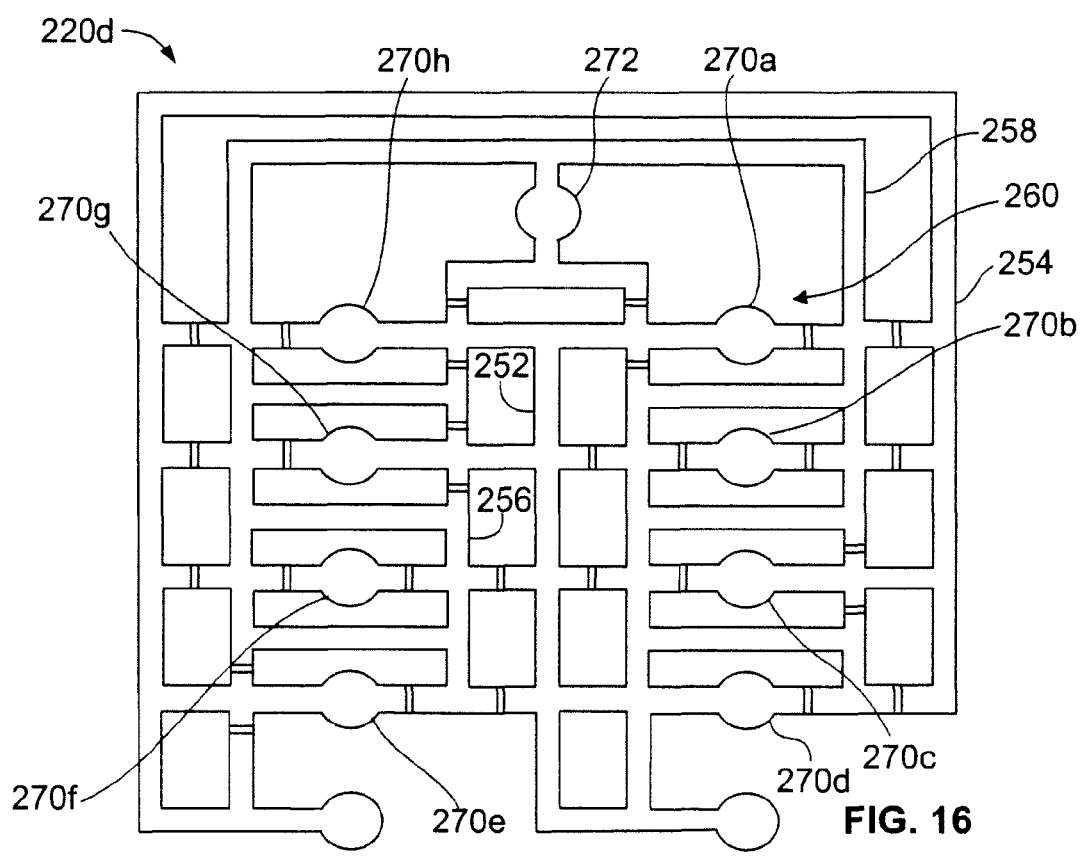

In FIG. 14, the contact area 272 of the auto-calibration label or circuit 220*b* is connected with the contact area 270*f* via the second auxiliary common connection 258. In FIG. 15, the contact area 272 of the auto-calibration label or circuit 220*c* is connected with the second common connection 254 via the second auxiliary common connection 258. In FIG. 16, the contact area 272 of the auto-calibration label or circuit 220*d* is connected with the first common connection 252 via the first and second auxiliary common connections 256, 258. It is contemplated that an auto-calibration circuit or label may have a contact area 272 that is connected to one or more of the isolated contact areas 270*b*, 270*f*.

It is also contemplated that the contacts areas may be in different locations. For example, the contact areas may be in a linear array.

Figure 17:
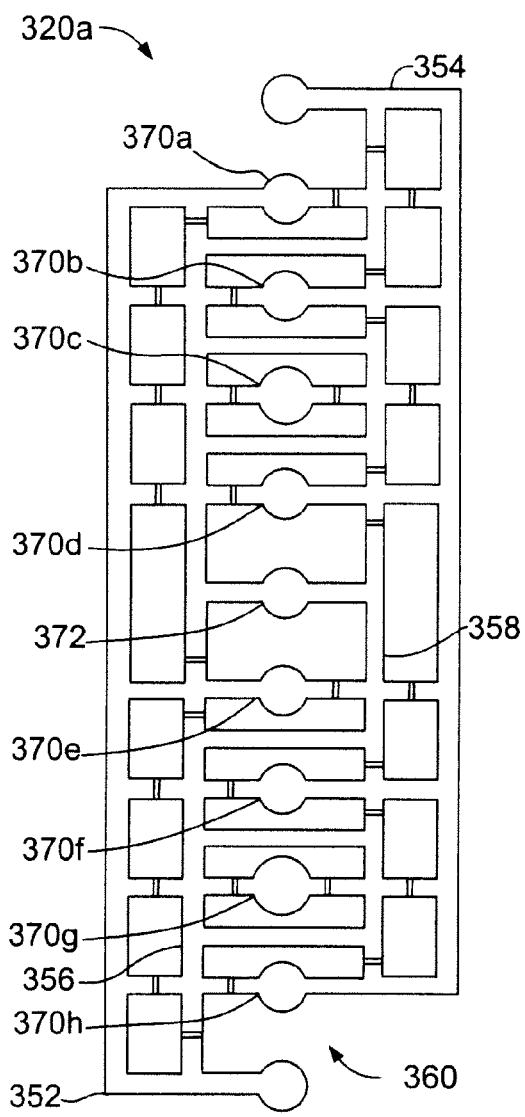
FIGS. 17-20 show coded auto-calibration circuits or labels according to another embodiment.

As shown in FIG. 17, the auto-calibration circuit or label 320*a* includes a first common connection 352, a second common connection 354, a first auxiliary common connection 356, a second auxiliary common connection 358 and a plurality of electrical connections 360. The plurality of electrical connections 360 includes a plurality of contact areas or pads 370*a-h*. The contact areas are positioned generally in a center line of the auto-calibration circuit or label 320*a*. It is contemplated that the contact areas 370*a-h* may be located in different positions than depicted in FIG. 17. The auto-calibration circuit or label 320*a* further includes a contact area or pad 372 that is located in the general center of the auto-calibration circuit or label 320*a*. It is contemplated that such a contact area or pad may be located in other areas of the circuit or label.

In the embodiment depicted in FIG. 17, the electrical connections 360 are capable to be routed directly from each of the contact areas 370 to a respective first common connection 352 or a second common connection 354. The information from the plurality of electrical connections 360 corresponds to the calibration information of the test sensor(s) to be used by the instrument or meter.

According to one aspect, substantially all of contact areas 370*a-h* are initially electrically connected to the first common connection 352 or the second common connection 354 in the auto-calibration circuit or label 320*a* of FIG. 17.

At least one of the contact areas 370 in one embodiment (e.g., contact areas 370*c*, 370*g* in FIG. 17) is isolated in that the contact area is not connected to any of the remaining contact areas 370. Since two isolated contacts areas are used (isolated contact areas 370*c*, 370*g* in FIG. 17), the spacing between these contact areas may be used as additional coding information. The distance between the isolated contact areas may be used, for example, to distinguish between different products. For example, if the isolated contact areas are directly adjacent to each other, then that may correspond to a first product. If the isolated contact areas are separated by one intervening contact area, then that may correspond to a second product. It is contemplated that the distance between the isolated contact areas may be used in another manner.

Referring still to FIG. 17, contact areas 370a, 370e are connected to the first common connection 352. The contact areas 370b, 370d, 370f and 370h are connected to the second common connection 354.

To expand the additional combinations, an additional second contact area that can function in a different manner than the other first contact areas may be included. This second contact area may be used to significantly enhance the amount of auto-calibration information that can be transferred to the instrument or meter. In one aspect, the second contact area may be connected to the first common connection, the second common connection, an isolated contact area, and/or connected to a plurality of isolated or no-contact areas. The second contact area may be connected to none of the other common connections and the isolated or no-contact areas.

Figure 18:
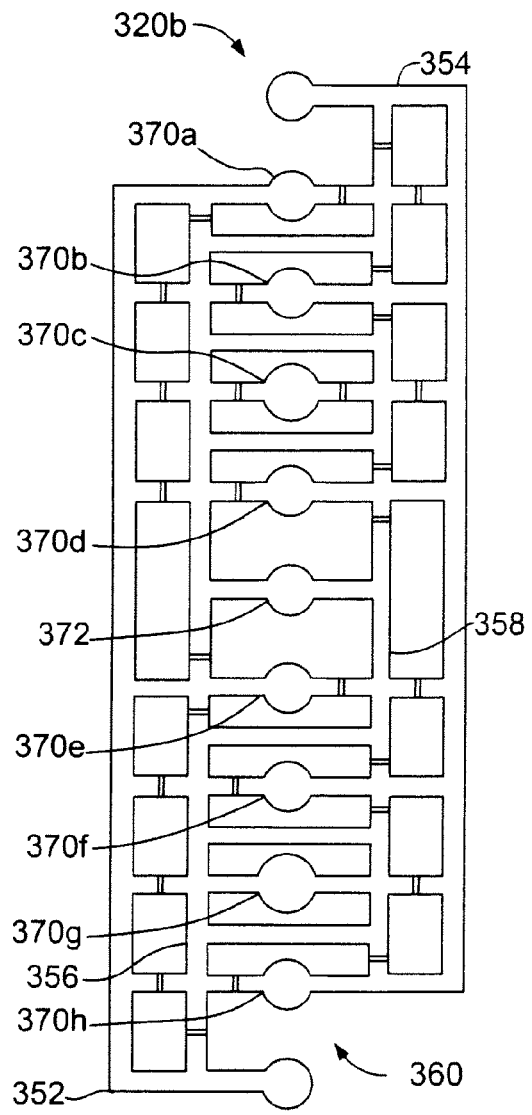
Figure 19:
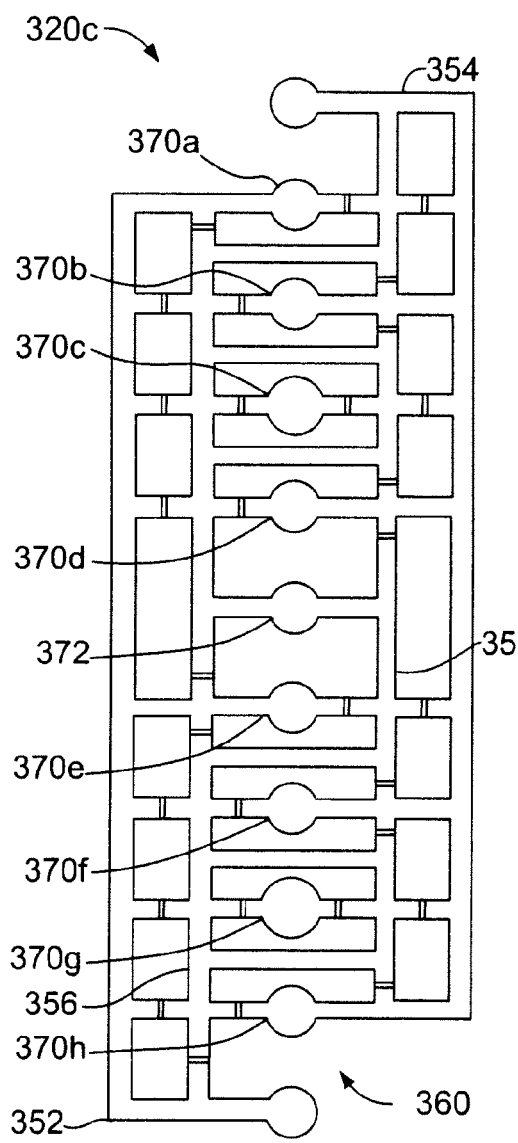
Figure 20:
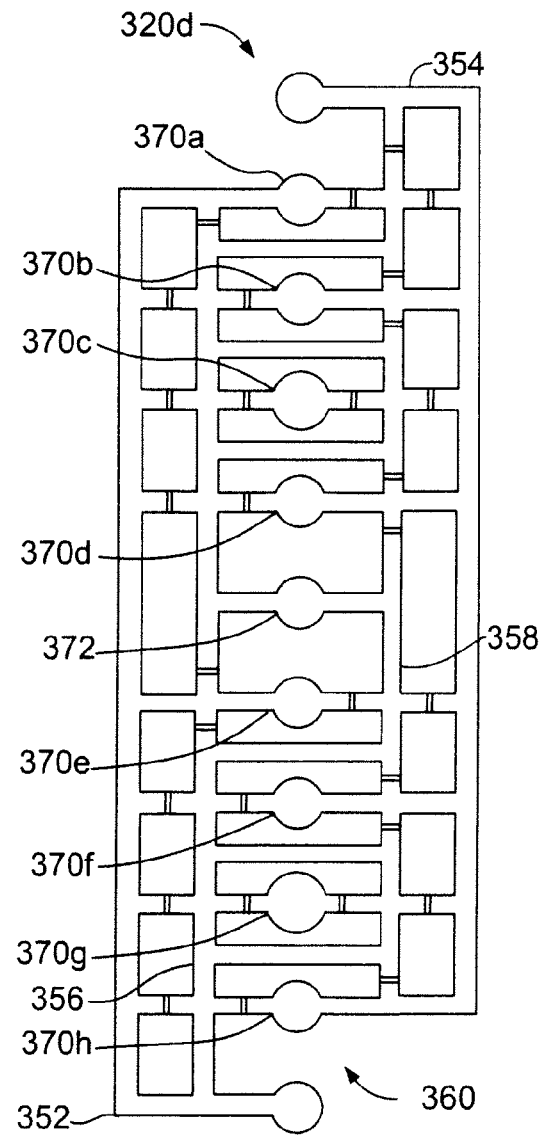

For example, the contact area 372 may be connected to the first common connection 352, the second common connection 354, the isolated contact area 370c, isolated contact area 370g, or connected to both the isolated contact areas 370c, 370g. In FIG. 18, the contact area 372 of the auto-calibration label or circuit 320b is connected with the contact area 370g via the first and second auxiliary common connections 356, 358. In FIG. 19, the contact area 372 of the auto-calibration label or circuit 320c is connected with the second common connection 354 via the first and second auxiliary common connections 356, 358. In FIG. 20, the contact area 372 of the auto-calibration label or circuit 320d is connected with the first common connection 352 via the first and second auxiliary common connections 356, 358. It is contemplated that an auto-calibration circuit or label may have a contact area 372 that is connected to one or more of the isolated contact areas 370c, 370g.

It is contemplated that the auto-calibration circuits or labels may be used with instruments other than instrument 10 depicted in FIGS. 1, 2 and 6. The auto-calibration circuits or labels may also be used in other type of sensor packs than sensor package 12 or test sensors. For example, the auto-calibration circuits or labels may be used in sensor packages such as a cartridge with a stacked plurality of test sensors or a drum-type sensor package.

Alternative Embodiment A

An auto-calibration circuit or label being adapted to be used with an instrument, the instrument being adapted to determine information related to an analyte of a fluid sample, the auto-calibration circuit or label comprising:
  a plurality of electrical connections conveying auto-calibration information corresponding to a test sensor, the auto-calibration information being adapted to be utilized by the instrument to auto-calibrate for the test sensor, the plurality of electrical connections including a plurality of first contact areas;
  a first common connection;
  a second common connection being separate and distinct from the first common connection;
  a first auxiliary common connection being separate and distinct from the first and second common connections; and
  a second auxiliary common connection being separate and distinct from the first and second common connections, the first and second auxiliary common connections being located on opposing sides of the plurality of contact areas,
  wherein the plurality of electrical connections is adapted to be routed directly from each of the plurality of first contact areas to a respective first common connection or a second common connection.

Alternative Embodiment B

The circuit or label of Alternative Embodiment A wherein a first one of the plurality of first contact areas is routed directly to the first common connection and a second one of the plurality of first contact areas is routed directly to the second common connection.

Alternative Embodiment C

The circuit or label of Alternative Embodiment A wherein at least one of the plurality of first contact areas is not routed to either the first common connection or the second common connection.

Alternative Embodiment D

The circuit or label of Alternative Embodiment C wherein at least two of the plurality of first contact areas are not routed to either the first common connection or the second common connection.

Alternative Embodiment E

The circuit or label of Alternative Embodiment C further including a second contact area, the second contact area being adapted to be electrically connected to one of the plurality of first contact areas that is not routed to either the first common connection or the second common connection.

Alternative Embodiment F

The circuit or label of Alternative Embodiment C further including a second contact area, the second contact area being adapted to be electrically connected to the first common connection, the second common connection, or at least one of the plurality of first contact areas that is not electrically connected to the first common connection or the second common connection.

Alternative Embodiment G

The circuit or label of Alternative Embodiment A further including a second contact area, the second contact area being located in a general center of the circuit or label.

Alternative Embodiment H

The circuit or label of Alternative Embodiment A wherein the auto-calibration circuit or label is generally circular shaped.

Alternative Embodiment I

The circuit or label of Alternative Embodiment A wherein the auto-calibration circuit or label is generally polygonal shaped.

Alternative Embodiment J

The circuit or label of Alternative Embodiment A wherein the first common connection is an inner ring and the second common connection is an outer ring.

Alternative Embodiment K

The circuit or label of Alternative Embodiment A wherein at least one of the first common connection and the second common connection is continuous.

Alternative Embodiment L

The circuit or label of Alternative Embodiment A wherein the first auxiliary common connection is an inner ring and the second auxiliary common connection is an outer ring.

Alternative Embodiment M

A test sensor adapted to determine information relating to an analyte of a fluid sample, the test sensor comprising:
  a base;
  a second layer in which the second layer and the base assist in forming a channel to receive the fluid sample;
  an auto-calibration circuit or label located on the base or the second layer, the auto-calibration circuit or label the auto-calibration circuit or label comprising:
    a plurality of electrical connections conveying auto-calibration information corresponding to a test sensor, the auto-calibration information being adapted to be utilized by the instrument to auto-calibrate for the test sensor, the plurality of electrical connections including a plurality of first contact areas;
a first common connection;
a second common connection being separate and distinct from the first common connection;
a first auxiliary common connection being separate and distinct from the first and second common connections; and
a second auxiliary common connection being separate and distinct from the first and second common connections, the first and second auxiliary common connections being located on opposing sides of the plurality of contact areas,
wherein the plurality of electrical connections is adapted to be routed directly from each of the plurality of first contact areas to a respective first common connection or a second common connection.

Alternative Embodiment N

The circuit or label of Alternative Embodiment M wherein the second layer is a lid.

Alternative Embodiment O

The circuit or label of Alternative Embodiment M further including a spacer, the spacer assisting with the lid and the base adapted to assist in forming a channel to receive the fluid sample.

Alternative Embodiment P

The circuit or label of Alternative Embodiment M further including a first electrode and a second electrode.

Alternative Embodiment Q

A sensor package adapted to be used in an instrument or meter to determine information relating to an analyte in a fluid sample, the sensor package comprising:
at least one test sensor being adapted to receive the fluid sample and being operable with the instrument; and
an auto-calibration circuit or label being located on the at least one test sensor comprising:
a plurality of electrical connections conveying auto-calibration information corresponding to a test sensor, the auto-calibration information being adapted to be utilized by the instrument to auto-calibrate for the test sensor, the plurality of electrical connections including a plurality of first contact areas;
a first common connection;
a second common connection being separate and distinct from the first common connection;
a first auxiliary common connection being separate and distinct from the first and second common connections; and
a second auxiliary common connection being separate and distinct from the first and second common connections, the first and second auxiliary common connections being located on opposing sides of the plurality of contact areas,
wherein the plurality of electrical connections is adapted to be routed directly from each of the plurality of first contact areas to a respective first common connection or a second common connection.

Alternative Embodiment R

The sensor package of Alternative Embodiment Q further including at least one cavity containing a respective one of the at least one test sensor, the at least one cavity being arranged around the auto-calibration circuit or label.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as shown in the attached claims.

What is claimed is:

1. An auto-calibration circuit or label being adapted to be used with an instrument, the instrument being adapted to determine information related to an analyte of a fluid sample, the auto-calibration circuit or label comprising:
a plurality of electrical connections conveying auto-calibration information corresponding to a test sensor, the auto-calibration information being adapted to be utilized by the instrument to auto-calibrate for the test sensor, the plurality of electrical connections including a plurality of first contact areas;
a first common connection;
a second common connection being separate and distinct from the first common connection;
a first auxiliary common connection being separate and distinct from the first and second common connections; and
a second auxiliary common connection being separate and distinct from the first and second common connections, the first and second auxiliary common connections being located on opposing sides of the plurality of contact areas,
wherein the plurality of electrical connections is adapted to be routed directly from each of the plurality of first contact areas to a respective first common connection or a second common connection.

2. The circuit or label of claim 1, wherein a first one of the plurality of first contact areas is routed directly to the first common connection and a second one of the plurality of first contact areas is routed directly to the second common connection.

3. The circuit or label of claim 1, wherein at least one of the plurality of first contact areas is not routed to either the first common connection or the second common connection.

4. The circuit or label of claim 3, wherein at least two of the plurality of first contact areas are not routed to either the first common connection or the second common connection.

5. The circuit or label of claim 3, further including a second contact area, the second contact area being adapted to be electrically connected to one of the plurality of first contact areas that is not routed to either the first common connection or the second common connection.

6. The circuit or label of claim 3, further including a second contact area, the second contact area being adapted to be electrically connected to the first common connection, the second common connection, or at least one of the plurality of first contact areas that is not electrically connected to the first common connection or the second common connection.

7. The circuit or label of claim 1, further including a second contact area, the second contact area being located in a general center of the circuit or label.

8. The circuit or label of claim 1, wherein the auto-calibration circuit or label is generally circular shaped.

9. The circuit or label of claim 1, wherein the auto-calibration circuit or label is generally polygonal shaped.

10. The circuit or label of claim 1, wherein the first common connection is an inner ring and the second common connection is an outer ring.

11. The circuit or label of claim 1, wherein at least one of the first common connection and the second common connection is continuous.

12. The circuit or label of claim 1, wherein the first auxiliary common connection is an inner ring and the second auxiliary common connection is an outer ring.

13. A test sensor adapted to determine information relating to an analyte of a fluid sample, the test sensor comprising:
   a base;
   a second layer in which the second layer and the base assist in forming a channel to receive the fluid sample;
   an auto-calibration circuit or label located on the base or the second layer, the auto-calibration circuit or label the auto-calibration circuit or label comprising:
   a plurality of electrical connections conveying auto-calibration information corresponding to a test sensor, the auto-calibration information being adapted to be utilized by the instrument to auto-calibrate for the test sensor, the plurality of electrical connections including a plurality of first contact areas;
   a first common connection;
   a second common connection being separate and distinct from the first common connection;
   a first auxiliary common connection being separate and distinct from the first and second common connections; and
   a second auxiliary common connection being separate and distinct from the first and second common connections, the first and second auxiliary common connections being located on opposing sides of the plurality of contact areas,
   wherein the plurality of electrical connections is adapted to be routed directly from each of the plurality of first contact areas to a respective first common connection or a second common connection.

14. The test sensor of claim 13, wherein the second layer is a lid.

15. The test sensor of claim 13, further including a spacer, the spacer assisting with the lid and the base adapted to assist in forming a channel to receive the fluid sample.

16. The test sensor of claim 13, further including a first electrode and a second electrode.

17. A sensor package adapted to be used in an instrument or meter to determine information relating to an analyte in a fluid sample, the sensor package comprising:
   at least one test sensor being adapted to receive the fluid sample and being operable with the instrument; and
   an auto-calibration circuit or label being located on the at least one test sensor comprising:
   a plurality of electrical connections conveying auto-calibration information corresponding to a test sensor, the auto-calibration information being adapted to be utilized by the instrument to auto-calibrate for the test sensor, the plurality of electrical connections including a plurality of first contact areas;
   a first common connection;
   a second common connection being separate and distinct from the first common connection;
   a first auxiliary common connection being separate and distinct from the first and second common connections; and
   a second auxiliary common connection being separate and distinct from the first and second common connections, the first and second auxiliary common connections being located on opposing sides of the plurality of contact areas,
   wherein the plurality of electrical connections is adapted to be routed directly from each of the plurality of first contact areas to a respective first common connection or a second common connection.

18. The sensor package of claim 17, further including at least one cavity containing a respective one of the at least one test sensor, the at least one cavity being arranged around the auto-calibration circuit or label.

19. The circuit or label of claim 1, wherein the auto-calibration circuit or label is a single layer.

20. The test sensor of claim 13, wherein the auto-calibration circuit or label is a single layer.

* * * * *